United States Patent [19]

Fujimori

[11] Patent Number: 4,492,469
[45] Date of Patent: Jan. 8, 1985

[54] SYSTEM FOR MEASURING THE PRESSURE SEALED INSIDE AN ENVELOPE

[75] Inventor: Yasutomo Fujimori, Yokohama, Japan

[73] Assignee: Tokyo Shibaura Denki Kabushiki Kaisha, Kawasaki, Japan

[21] Appl. No.: 375,225

[22] Filed: May 5, 1982

[30] Foreign Application Priority Data

May 20, 1981 [JP] Japan .................................. 56-74850

[51] Int. Cl.³ .............................................. G01B 9/02
[52] U.S. Cl. .................................................... 356/361
[58] Field of Search ................. 356/359, 360, 361, 362

[56] References Cited

U.S. PATENT DOCUMENTS 3,625,616 12/1971 Lee ...................................... 356/361
4,452,071 6/1984 Eesley et al. .................... 356/361 X

OTHER PUBLICATIONS

Carnevale et al., "Spatial Coherence Analysis by Interferometric Methods", *Optica Acta*, vol. 24, No. 11, pp. 1099-1104, Nov. 1977.
The Review of Scientific Instruments, vol. 37, No. 4, Apr. 1966, pp. 452-455.
Dictionary "Der Grosse Brockhaus", 18th edition, vol. 4, 1978, p. 575.

Primary Examiner—Davis L. Willis
Assistant Examiner—Matthew W. Koren
Attorney, Agent, or Firm—Oblon, Fisher, Spivak, McClelland & Maier

[57] ABSTRACT

In a system for measuring the pressure of a gas sealed in a lamp, a laser beam emitted from a laser unit and converged by a convergent lamp is split by a first half mirror into first and second laser beams. The first laser beam is focused to a focal point of the lens close to the filament of the lamp, diverged from this focal point, and reflected by a first mirror toward a second half mirror. The second laser beam is reflected by a mirror toward the second half mirror. At the second half mirror, both laser beams are combined and converted into interfered light. The interfered light is projected to an aperture which transmits the light rays within half fringe of interference. The light rays become incident on a photodetector. When the lamp is energized, the interference fringes change during a predetermined period of time, and signals of light and dark levels are alternately detected by the photodetector. The signals output by the photodetector are processed during a predetermined period of time. On the basis of the interference order data obtained, the gas pressure inside the lamp is calculated according to a predetermined equation.

7 Claims, 2 Drawing Figures

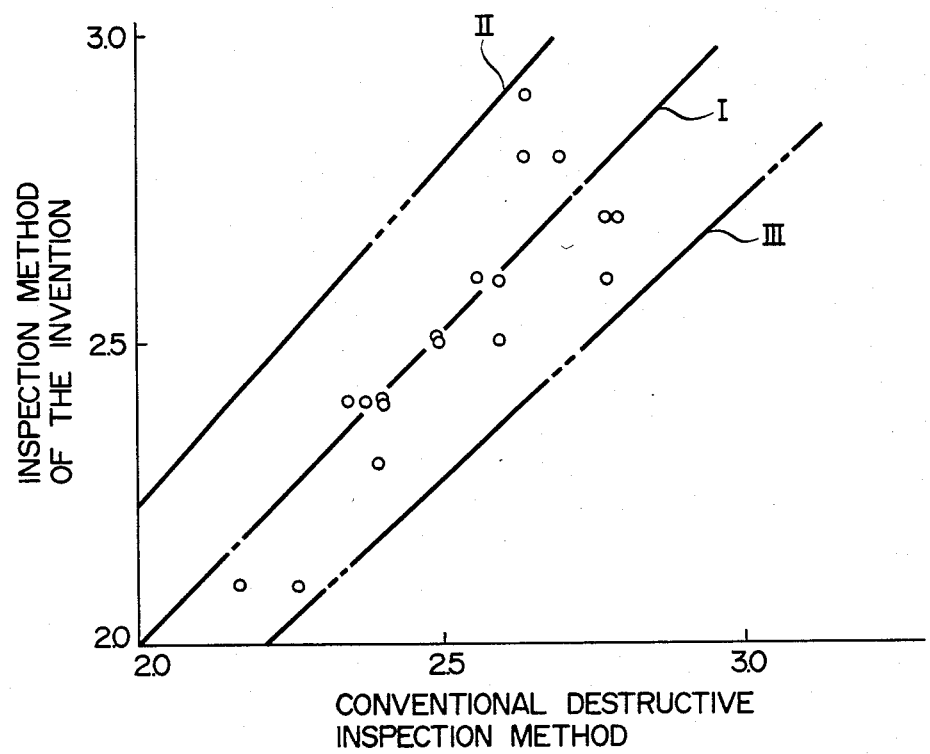
F I G. 2

SYSTEM FOR MEASURING THE PRESSURE SEALED INSIDE AN ENVELOPE

BACKGROUND OF THE INVENTION

The present invention relates to a system for measuring the pressure sealed inside an envelope of a lamp and, more particularly, to a system for optically measuring the pressure of a gas sealed in a lamp without requiring destruction of the lamp.

An inert gas such as argon, xenon and krypton is filled to a predetermined pressure inside a lamp. When the pressure of the gas sealed in the lamp is higher than a predetermined pressure, the lamp may break down during operation. On the other hand, when the pressure of the gas is lower than the predetermined pressure, the life time of the lamp is shortened. Therefore, it is necessary to check the pressure of the gas in the lamps after manufacturing them. As a method for measuring the pressure of the gas in the lamp, the so-called destructive inspection method is known. According to this destructive inspection method, a lamp is destroyed in water, the gas inside the lamp is collected under atmospheric pressure, and the volume of the gas is measured. The internal volume of the lamp is measured by another method. The pressure of the gas in units of atmospheres is calculated from the ratio of the internal volume of the lamp to the volume of the gas. Since the lamp is destroyed in this destructive inspection method, this method cannot be applied to all the lamps which are manufactured. For this reason, only some lamps are sampled and the gas pressure of the other lamps is assumed statistically from the gas pressure of the sampled lamps. Especially, all the lamps that are made by the existing manufacturing lines cannot have the same gas pressure desired. Some lamps having a gas pressure much different from the predetermined pressure may be manufactured. In the past, there have been cases wherein lamps sealed with gas under abnormal pressures were manufactured, which resulted in serious accidents.

In this way, according to the destructive inspection method, lamps of abnormal gas pressure alone cannot be segregated, and the conventional pressure test cannot be performed for all the lamps manufactured.

SUMMARY OF THE INVENTION

It is an object of the present invention to provide a system for correctly measuring the pressure of a gas sealed in an envelope of a lamp without requiring destruction of the envelope having a heat source therein.

The present invention provides a system including an interferometer. In the interferometer, a coherent light beam is split into first and second light beams which are combined to interfere. The first light beam is converged to the convergent point from which it is diverged. The envelope is located in the optical path of the first light beam so that the heat source inside the envelope is located in the vicinity of the convergent point. Then, changes in the interference fringes after the heat source of the envelope is energized until a certain period of time elapses are read out. The pressure of the gas inside the envelope is obtained from the change in the order of interference.

BRIEF DESCRIPTION OF THE DRAWINGS

FIG. 2 is a graph showing comparison of data obtained by the conventional destructive inspection method and the system shown in FIG. 1.

DETAILED DESCRIPTION OF THE PREFERRED EMBODIMENT

Figure 1:
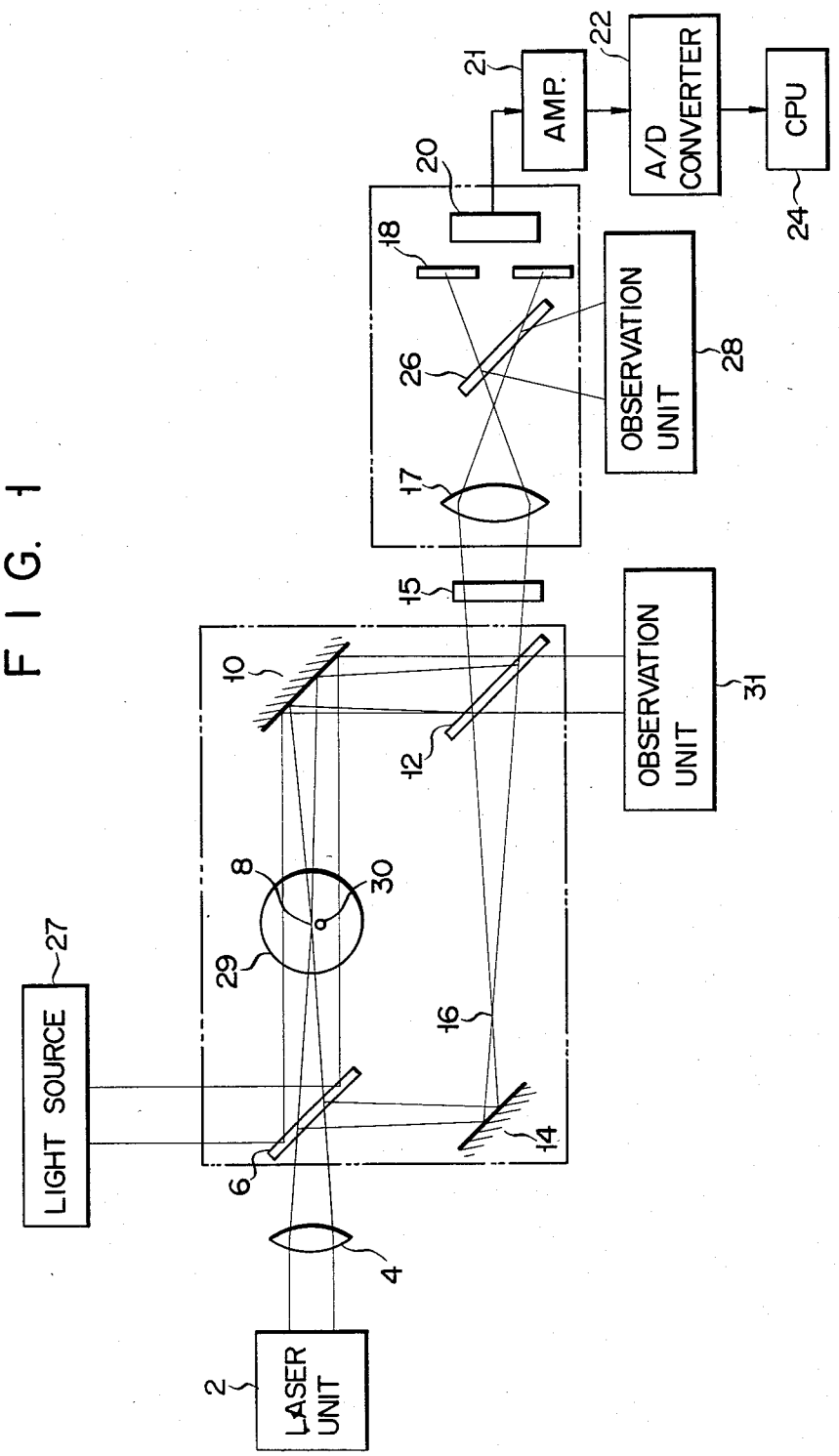
FIG. 1 is a block diagram of a system for measuring the pressure of a gas sealed in an envelope of a lamp according to an embodiment of the present invention.

A system for measuring the pressure of a gas sealed in a lamp according to an embodiment of the present invention will be described with reference to FIG. 1. A laser beam emitted from an He-Ne laser unit 2 having an output of about 1 mW is directed to a convergent lens 4. The convergent lens 4 converges the incident light beam and the converged light beam becomes incident on a first half mirror 6. The first half mirror 6 splits the incident light beam into a first laser beam which is transmitted through the mirror 6 and a second laser beam which is reflected by the mirror 6. After being focused on a focal point 8, the first laser beam is diverged, reflected by a first mirror 10, and is directed to a second half mirror 12. After being reflected by a second mirror 14 and focused on a focal point 16, the second laser beam is similarly directed to the second half mirror 12. The optical path of the first laser beam leading from the first half mirror 6 via the first mirror 10 to the second half mirror 12 has substantially the same length as the second optical path of the second laser beam leading from the first half mirror 6 via the second mirror 14 to the second half mirror 12, thus establishing a laser interferometer. The substantially same length herein allows an error of 5 to 10 mm in the laser unit which is a He-Ne laser unit. A narrow band filter 15 for passing light of the wavelength of the laser beam alone is arranged in the traveling path of the laser beam interfered at the second half mirror 12, that is, the common optical path of the first laser beam reflected by the second half mirror 12 and the second laser beam transmitted by the first half mirror 6. The interference laser beam transmitted through the narrow band filter 15 is projected through a projection lens 17 onto an aperture 18 for transmitting only light components within ½ fringe of the coherent laser beam. A photodetector 20 for detecting the light components of the coherent laser beam at the aperture 18 is arranged behind the aperture 18. An amplifier 21 is connected to the photodetector 20. A detected signal amplified by the amplifier 21 and having an alternate waveform like a sine waveform is supplied to an A/D converter 22. The A/D converter 22 converts the analog coherent signal into a digital signal which is supplied to a CPU 24.

A third half mirror 26 is arranged between the projection lens 17 and the aperture 18. The third half mirror 26 splits the coherent laser beam into two light beams; one is transmitted to the aperture 18 described above and the other is reflected toward an observation unit 28, for example, a TV camera or a screen. The interference fringes can be observed through the observation unit 28.

A lamp 29 whose gas pressure is to be measured is arranged in the optical path of the first laser beam between the first half mirror 6 and the mirror 10, so that a filament 30 thereof is close to the focal point, preferably, just above the focal point of the convergent lens 4. A light source 27 for emitting incoherent light and for illuminating the lamp is provided. When the light source 27 is energized, the incoherent light from the light source 27 is reflected by the half mirror 6 and the filament 30 of lamp is illuminated. Then, the incoherent light containing the image information of the filament 30 is projected onto an observation unit 31 through the second half mirror 12. The image of the filament 30 is observed through the observation unit 31, for example, a TV camera or a screen to see if the filament 30 is correctly located at the focal point.

For the following reason, the filament 30 of the lamp 29 is arranged near the focal point of the convergent lens 4. The lamp 29 has a tube which, in turn, has a substantially circular section as shown in FIG. 1. When the beam consisting of parallel light rays or a divergent beam becomes incident on the tube of the lamp having the circular section, the incident light beam is refracted by the tube of the lamp 29. Then, the light rays of the incident beam may be deviated in various direction or the phases of the light rays may be changed from one light ray to another. When the convergent light beam is incident on the tube of the lamp 29, the beam spot projected on the lamp housing can be sufficiently small relative to the lamp housing. Therefore, the beam spot area of the lamp housing can be considered as a prism so that the laser beam is deviated in a predetermined direction but the phase of the light rays may not be changed substantially. The filament 30 of the lamp 29 is located in the vicinity of the focal point 8, preferably just below the focal point 8 as shown in FIG. 1, because the temperature change is the strongest just above the filament 30 when the lamp 29 is energized. Therefore, the difference in the optical path when the lamp 29 is energized and when the lamp 29 is not energized is greatest at this point, so that detection of the gas pressure inside the lamp 29 may be most correctly performed at this point.

If the lamp 29 is located in the optical path of the first laser beam, the first and second laser beams interfere with each other by means of the second half mirror 12, and the interference fringes are observed by the observation unit 28 through the filter 15, the projection lens 17, and the third half mirror 26. Furthermore, the light information of light, dark, or grey produced from the interference is projected on the photodetector 20 through the aperture 18. Therefore, in correspondence with the grey, light or dark light information depending upon the optical path difference of the first and second laser beams and the position of the aperture 18, an intermediate, low or high level signal is supplied to the amplifier 21. Since the interior of the lamp 29 is kept at ambient temperature unless the lamp 29 is energized, the length of the optical path inside the lamp 29 does not change. Therefore, the photodetector 20 continues to output a signal of intermediate, high or low level. When the lamp 29 is energized, the temperature of the interior gas of the lamp 29 rises, and the length of the optical path in the lamp 29 changes. Therefore, the phase of the first laser beam incident on the half mirror 12 through the first half mirror 6 and the mirror 10 changes. The first laser beam with the changed phase interferes with the second laser beam having the unchanged phase at the second half mirror 12. The order of interference changes during the process of transit from the state in which the lamp 29 is deenergized to the state in which the lamp 29 is energized. Thus, the light information of grey, light, grey and dark are alternately supplied to the photodetector 20. Accordingly, the photodetector 20 alternately supplies to the amplifier 21 signals of intermediate, high, intermediate and low levels, that is, interference signals like sine waves. These interference signals are converted into digital signals by the A/D converter 22. Let m denote the order of interference from the time the lamp 29 is energized until T seconds elapse, and P denote the pressure of the gas inside the lamp 29. Then, a refractive index $n_0$ of the gas at ambient temperature (25° C.) and at a pressure $P_0$, an inner diameter $l$ of the lamp 29, a wavelength $\lambda$ of the laser beam, and a proportional constant $\eta$ hold the relation below:

$$1/\eta \cdot m \cdot \lambda \cdot 1/l = (n_0 - 1) \cdot P/P_0$$

T is a duration of time which is within one second and is fixed for lamps of the same kind and under the same conditions. The proportional constant $\eta$ is the same for lamps of the same kind and is determined depending upon the shape, position and size of the filament. This proportional constant $\eta$ is calculated in advance by obtaining an actual pressure $P'$ of a particular lamp of which the order m of interference is known by the conventional destructive inspection method as described above and substituting the obtained value of $P'$ in the relation above. For example, with a halogen lamp having a relatively small diameter such as 6 mm inner diameter, $\eta \cong 0.8$ and $T \cong 0.1$ sec.

The order m of interference is not limited to an integer. The interference signal like sine wave is processed in the CPU 24. Within one fringe are read out, from the interference signal, a signal of high level corresponding to light, a signal of low level corresponding to dark, and two signals of intermediate level corresponding to grey between light and dark. Thus, the order m of ¼ fringe is obtained. The data obtained by the order m of ¼ fringe is shown in FIG. 2 which will be described later.

Then, the pressure P can be sequentially calculated in accordance with detection signals of the order m of interference for each lamp to be measured, if a function $P \cong m \cdot \alpha$ is input in advance to the CPU 24, which is obtained by substituting lamp diameter $l$, wavelength $\lambda$ of the laser beam, $n_0$, and $\eta$.

FIG. 2 shows measurements obtained by the system according to the present invention as a ratio to those obtained by the conventional destructive inspection method. Referring to FIG. 2, curve I is a reference curve corresponding to ratio 1 as described above while curves II and III correspond to errors of ±10% from reference curve I. As may be seen from FIG. 2, the measurements according to the embodiment of the present invention are bounded within curves II and III, indicating that the present invention provides satisfactory effects. In this case, the measurement precision is less than 0.2 atm although not shown in the graph of FIG. 2.

In this manner, the pressure of the gas sealed in a lamp or the like may be measured utilizing the heating function of a heating part which is always incorporated in the lamp and also utilizing an interferometer, without requiring destruction of the lamp.

Since the pressure of the gas sealed in the lamp can be measured without impairing the original function of the lamp, all the lamps manufactured may be subjected to the measurements. The pressure data obtained may be attached to the lamps which facilitate evaluation of the properties of the lamps such as life time.

In the embodiment described above, a description has been made with reference to a system for measuring the pressure of a gas sealed within a lamp. However, the present invention is not limited to this, and may be applied to measurement of the gas inside any envelope having a heating body.

What is claimed is:

1. A system for measuring a pressure of a gas contained in a lamp having a heat source in the form of a filament comprising:

emitting means for emitting a coherent light beam;

splitting means for splitting the coherent light beam into a first and second light beam;

means for conversion at least said first light beam towards a conversion point;

means for subjecting to interference said first light beam diverse from said conversion point and said second light beam, and for producing light containing information of the interference fringes;

reading means for reading from the received interferred light a change a number of order of interference which is caused by interference during a predetermined period of time after said filament of said lamp arranged near said conversion point is energized;

calculating means coupled to said reading means for performing an operation according to the relationship of:

$$P \cong \frac{m\lambda}{\eta l(n_o - 1)} \cdot P_o$$

where m is the order of interference change which is not limited to an integer, $\lambda$ is a wavelength of a coherent light beam, l is an inner diameter of said lamp, $n_0$ is a refractive index of said gas at ambient pressure $p_0$ and $\eta$ is a proportional constant.

2. A system according to claim 1, wherein said reading means comprises means for receiving the interfered light and extracting light rays within ½ fringe from the interfered light, and means for detecting the light rays and for generating an interference signal.

3. A system according to claim 1, wherein said reading means includes a filter for transmitting the interfered light of a predetermined wavelength alone.

4. A system according to claim 1, further including means for observing said heat source in said envelope to be disposed at the convergent point.

5. A system according to claim 4, wherein said observing means includes a incoherent light source for illuminating the heat source.

6. A system according to claim 1, further comprising means for observing the interference fringes.

7. A system according to claim 1, wherein the predetermined period of time is within 1 second.

* * * * *